United States Patent [19]

Delaune et al.

[11] Patent Number: 5,447,052
[45] Date of Patent: Sep. 5, 1995

[54] MICROWAVE HYDROCARBON GAS EXTRACTION SYSTEM

[75] Inventors: Patrick L. Delaune; Scott A. Hanson, both of Houston; Howard L. McKinzie, Sugar Land; Alan C. Wright, Bellaire, all of Tex.

[73] Assignee: Texaco Inc., White Plains, N.Y.

[21] Appl. No.: 172,793

[22] Filed: Dec. 27, 1993

Related U.S. Application Data

[63] Continuation-in-part of Ser. No. 979,953, Nov. 23, 1992, abandoned.

[51] Int. Cl.[6] .................. G01N 30/12; H05B 6/64
[52] U.S. Cl. .................. 73/19.09; 73/19.12; 422/78; 95/178; 95/254; 436/177
[58] Field of Search .............. 73/19.09, 19.12, 19.02, 73/31.07, 863.11, 863.12, 153; 55/267; 96/218; 95/178, 241, 254, 184, 251, 288; 422/285, 78, 298, 307; 436/155, 177, 181

[56] References Cited

U.S. PATENT DOCUMENTS

| | | | |
|---|---|---|---|
| 3,118,299 | 1/1964 | Worthington | 73/19.09 |
| 3,418,841 | 12/1968 | Issenmann | 73/19.09 |
| 3,616,375 | 10/1971 | Inoue | 204/162 R |
| 3,959,341 | 5/1976 | Dunn | 73/23.2 X |
| 4,304,609 | 12/1981 | Morris | 134/19 |
| 4,347,216 | 8/1982 | Kawasaki et al. | 422/78 |
| 4,453,319 | 6/1984 | Morris | 34/1 |
| 4,861,556 | 8/1989 | Neas et al. | 422/78 |
| 5,230,865 | 7/1993 | Hargett et al. | 422/78 |

*Primary Examiner*—Hezron E. Williams
*Assistant Examiner*—Michael J. Brock
*Attorney, Agent, or Firm*—James L. Bailey; Kenneth R. Priem; William J. Beard

[57] ABSTRACT

A method and apparatus for extracting hydrocarbon gas from drilling fluid samples utilizes microwave energy as the source for heating a sample, containing water, sufficiently to cause the extraction of the hydrocarbon gases therefrom. Either a batch or a continuous operation can be realized using this method.

5 Claims, 1 Drawing Sheet

MICROWAVE HYDROCARBON GAS EXTRACTION SYSTEM

CROSS REFERENCE TO RELATED PATENT APPLICATION

The present application is a continuation-in-part of our earlier patent application Ser. No. 07/979,953, filed Nov. 23, 1992 now abandoned.

BACKGROUND OF THE INVENTION

1. The Field Of The Invention

The present invention pertains to the method and apparatus for effecting a rapid extraction of hydrocarbon gases entrained in drilling fluids for analysis and in particular to the use of microwave energy in such method and apparatus.

2. The Prior Art

One state of the art method and apparatus uses a steam boiler to separate hydrocarbon gases from drilling fluids for the purpose of measuring and analyzing the gas content of the fluid. Drilling fluid, containing dissolved and or dispersed gases, is injected into a steam-mud mixing chamber. Steam is bubbled through a measured sample of drilling fluid and strips the hydrocarbons from the drilling fluid. The steam and the hydrocarbon gases are then collected in a condensing chamber. After a minimum of three minutes, the gas is withdrawn through a septum into a syringe and then injected into a gas chromatograph which determines the composition of the gas in the drilling fluid. Examples of these types of devices can be found in U.S. Pat. Nos. 2,341,169 and 3,050,449.

An alternative to the steam boiler is a mechanical agitation device which separates hydrocarbon gases from drilling fluid for the purposes of measurement and analysis. The analysis of these gases can be used to help determine the possibility of recovering gas and/or oil from any particular formation encountered during drilling.

In a drilling operation, drilling fluid is pumped down a drill pipe and out into an annulus between the pipe and hole or casing walls via openings in a drill bit. This drilling fluid carries up to the surface cuttings from the rock being drilled as well as any hydrocarbon gases which were trapped in the formation. When this drilling fluid reaches the surface, it is piped down a flow line into a shaker tank and then over a shale shaker (screen) where the rock cuttings are removed from the drilling fluid.

The conventional practice is to mount a mechanical agitator or gas trap in the shaker tank where it continuously extracts a portion of the entrained gases from the drilling fluid. These gases are then drawn from a head space of the gas trap, via a vacuum line, into a total gas analyzer and a gas chromatograph where the gases are analyzed for hydrocarbon content. Analysis of the recovered gases can be used to help determine the possibility of recovering gas or oil from the particular formation and to provide a warning of dangerous under balanced drilling conditions indicated by an increased gas level reading. An example of this type of apparatus can be found in Canadian Patent No. 2,006,766.

Some of the shortcomings of the steam still method of extraction of the hydrocarbon gases are that: it is relatively expensive and difficult to build; the steam boiler needs to be refilled with water periodically causing the still to cool and requiring a lengthy time period for it to return to operating temperature and pressure; the presence of active steam makes routine maintenance, such as changing septums or drain hoses, very difficult and dangerous; distilled water must be used to prevent the build up of scale and other deposits; the steam totally destroys the sample; and the gas extraction procedure is lengthy adding to the reluctance of rig site personnel to use this device.

Some of the shortcomings with the mechanical agitation type traps are: no existing gas traps are one hundred percent (100%) efficient at extracting gas from the drilling fluid; most traps used today have no way of relating observed gas in the sample line to the actual gas content of the drilling fluid, due to uncontrolled air dilution caused by air and gas leaks through the fluid exhaust port, which is generally open to air outside the trap, and leakage around the motor shaft stirrer bar; and most traps today experience changes in extraction efficiency which changes with the level of immersion in the drilling fluid. Normal rig operating conditions involve frequent changes in drilling fluid circulation rate which in turn changes the immersion level of the trap. Hence changes in gas concentration in the sample line can result from changes in rig operating conditions rather than changes in the amount of gas in the drilling fluid.

In order to relate the gas in a sample line to the actual gas in the drilling fluid, samples of the drilling fluid must be collected periodically and processed using a device which can extract virtually one hundred percent (100%) of the dissolved gas from the fluid. This gas is then manually injected into a gas chromatograph for analysis. This method is only effective in an gas trap system which is not sensitive to immersion level changes and where no uncontrolled dilution of the air and gas is allowed to occur so that it is possible to calibrate the gas trap.

The present invention utilizes microwave energy to heat and separate any dissolved and or entrained gases which may be present in drilling fluid under test. A microwave source has the advantage that it does not require warmup or special preparation, such as with the above mentioned boiler of a steam still. A gas extraction device utilizing microwave energy is faster, safer and easier to use than the currently available devices for removing the hydrocarbon gases from drilling fluid.

SUMMARY OF THE INVENTION

In a batch operating embodiment of the present invention, water and a sample of drilling fluid, containing solids and hydrocarbon gases, are injected into a gas tight chamber where microwave energy is used to heat the fluid causing the water to turn to steam and aid in the heating and separation of the lighter hydrocarbon gases. The separated gases are withdrawn from the chamber and inserted into a gas chromatograph for analysis.

In a continuous operating embodiment of the present invention, water and drilling fluid containing solids and hydrocarbon gases are pumped through a coil or chamber where microwave energy is used to heat and extract the lighter hydrocarbon gases in the same fashion as in the batch embodiment. The separated gases are then drawn into a gas chromatograph for analysis. Since the microwave extraction is virtually one hundred percent (100%) efficient, this method eliminates the need for periodically analyzing drilling fluid samples to calibrate the gas trap. A second continuous microwave gas sampling system could also be placed near a suction line where it would be used to measure recirculated gas in the drilling fluid. By setting the vacuum (the gas sample) rate equal to the drilling fluid volume rate circulating through the microwave chamber, the present invention can perform a direct percentage volume measurement of hydrocarbon gas in the drilling fluid.

BRIEF DESCRIPTION OF THE DRAWINGS

The present invention will now be described, by way of example, with reference to the accompanying drawings in which.

DETAILED DESCRIPTION OF THE PREFERRED EMBODIMENTS

Figure 1:
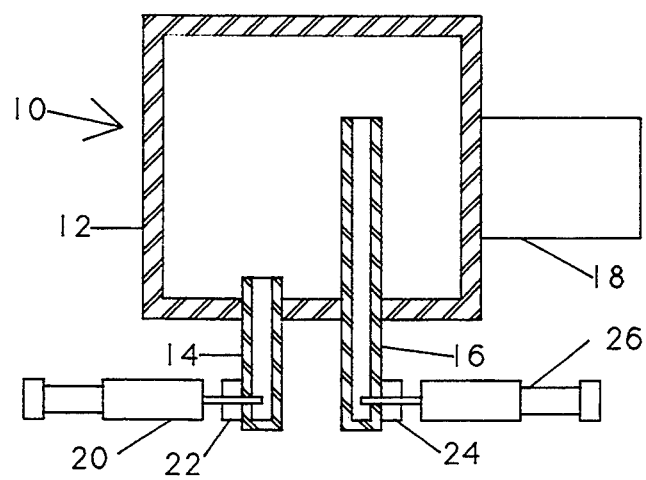
FIG. 1 is a schematic diagram, partially in section, of a batch sampling first embodiment of the present invention.

The batch sampling first embodiment 10 of the subject microwave hydrocarbon gas extraction system has an airtight chamber 12 with two tubes 14, 16 attached thereto and opening into the chamber. The chamber 12 and tubes 14, 16 must be made of microwavable material, such as teflon. One of these tubes 14 is used for injecting the drilling fluid sample and the other tube 16 is used for extracting the hydrocarbon gas sample. The gas sample extraction tube 16 extends to near the top of the inside of the chamber 12 to prevent any of the drilling fluid sample from entering the gas sample extraction tube. The chamber 12 is mounted in close proximity to a microwave source 18, for example inside a microwave oven (not shown) with the injection and extraction tubes extending outside of the oven.

The sample chamber is first cleaned by insertion of an adequate amount of water, generally an amount of water substantially equal to the amount of sample to follow. These amounts will, of course, be largely determined by the size of the chamber. Drilling fluid is injected into the sample chamber 12 via syringe 20, septum 22, and injection tube 14. Microwave energy is applied to the sample for a determined time at a determined power. As the water and gases are heated and separate from the drilling fluid, the steam and gases move through the chamber to the gas sample extraction tube 16, which is fitted with a septum 24. A second syringe 26 is inserted through the septum 24 and the gases are collected inside syringe 26. The gas sample is then injected into a gas chromatograph (not shown) for analysis. The gas sample syringe can be cooled in a water bath (also not shown) to condense the steam withdrawn from the sample chamber along with the released gases. The sample chamber 12 is then cleared and purged of fluid by adding water, which need not be distilled but could even be sea water, and then air via the injection tube 14. The septums 22, 24 are shown for convenience only in connection with the syringes. Clearly any known air-lock type of device could be used for inserting the fluid sample and withdrawing the gas.

The present invention does not require the use of distilled water to operate. This has been an inconvenient requirement of the prior art steam stills in order to prevent the build up of scale. The present invention also does not destroy the drilling fluid sample, which may be returned to the drilling system. This eliminates the previous problem of how to deal with the destroyed sample fluid which cannot be returned to the system but must be disposed somehow.

The steps of the subject process are as follows:

1) The sample chamber is empty and the microwave is off.

2) Water is injected into the sample chamber and the microwave is turned on.

3) The water is heated and purges the sample chamber with steam.

4) The fluid sample is injected into the hot steamy chamber followed by a water chaser of approximately equal volume.

5) The microwave source energized, for example, for 40 seconds at a power of 575 watts. Gas and steam thus generated are collected in the sample syringe outside the microwave oven. The microwave time is dependent upon the sample volume and the power output of the microwave unit.

6) The microwave is turned off and the sample syringe is removed from the extraction tube.

7) The sample tube is purged of fluid by adding water and then air via the extraction tube.

Prior to the present invention the steam still was the accepted best mode of extracting hydrocarbon gases from drilling fluids. What previously took approximately three minutes in a steam still now can be accomplished in a matter of seconds by the present invention. In addition to being faster, the present invention is safer and easier to use and also provides better gas extraction than the steam still method.

Figure 2:
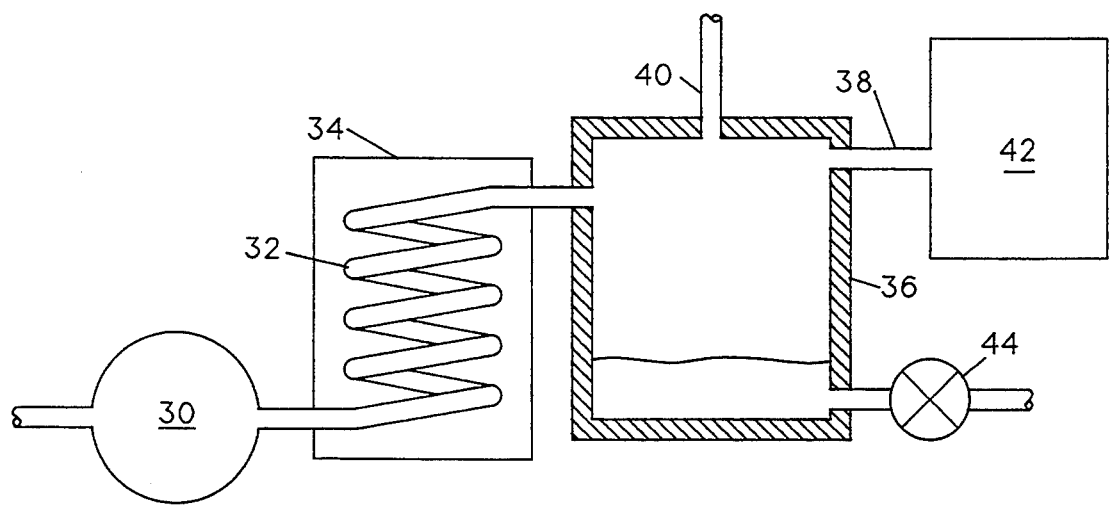
FIG. 2 is a diagrammatic side elevation, partially in section, of a continuous sampling second embodiment of the present invention.

Turning now to FIG. 2, the continuous gas sampling second embodiment is made up of a positive feed mechanism 30, such as a pump, which circulates drilling fluid and drill solids through a sample heating section 32, here shown in coil form, where it is exposed to microwave energy from a source 34. As the sample moves through the heating section 32, the microwave energy heats the drilling fluid and separates the hydrocarbon gases. Additionally, the heated drilled solids will release gas contained therein and further add to the quantitative extraction of all the gases from the borehole volume drilled. The heated fluid and gases then move into a cooling chamber 36 where the steam condenses and drops out along with the drilled solids and the drilling fluid. A vacuum line 38 and vent line 40 are attached to the cooling chamber and the gases are drawn into a gas chromatograph 42 at a known flow rate. The gases are analyzed and measured and then multiplied by the ratio of the vacuum rate to drilling fluid sample volume pump rate in order to determine the volume percent of gas in the drilling fluid. In most cases, however, the vacuum rate and drilling fluid sample pump rate will be equal so that the measurement directly reflects volume percentage of gas in the drilling fluid with no additional calculations. This is a capability that is not available in current gas extraction systems because of the variation in gas extraction efficiency which changes in drilling fluid rheology. The drilling fluid is drained from chamber 36 through valve 44. The continuous microwave gas extraction system of the present invention can be placed at a shale shaker to extract gas from the drilling fluid coming out of the hole and at a suction pit near the suction line to extract the gas recirculated with the drilling fluid being pumped down the hole during drilling operations.

The present invention may be subject to many modifications and changes without departing from the spirit or essential characteristics thereof. The present embodiments are therefore to be considered in all respects as illustrative and not restrictive of the scope of the invention.

We claim:

1. A method for extracting and analyzing hydrocarbon gas from drilling fluid comprising the steps of:
   providing a gas tight container having drilling fluid insertion means comprising a first air lock, gas collection means comprising a second air lock, and microwave energy generating means;
   steam purging said container; inserting a sample of drilling fluid into said container through said first air lock; subjecting said sample to microwave energy of sufficient power to microwave energy of sufficient power and duration to convert water contained therein to steam and to heat said fluid sample causing hydrocarbon gases contained therein to be driven off by said steam;
   collecting said hydrocarbon gases through said second air lock; and
   introducing said hydrocarbon (gas) gases to a gas chromatograph for analysis whereby the hydrocarbon gases can be measured without destroying the fluid sample.

2. The method according to claim 1 further comprising the step of:
   subsequent to the step of inserting a sample of drilling fluid but prior to said step of subjecting said sample to microwave energy, performing the step of inserting a volume of water substantially equal to said drilling fluid sample into said chamber 3. An apparatus for extracting and analyzing hydrocarbon gas in drilling fluid comprising:
   containing means having a gas tight sample receiving chamber therein;
   first air lock means to introduce a drilling fluid sample to said chamber;
   a microwave energy source;
   means to divert microwave energy from said source to said chamber to heat a drilling fluid sample inserted therein;
   second air lock means to collect gases released from said heated drilling fluid into said chamber and feed said gases to a gas chromatograph for analysis whereby said gases are removed from the drilling fluid sample for testing without destroying the drilling fluid sample.

4. An apparatus according to claim 3 wherein said containment means is formed of microwavable material.

5. An apparatus according to claim 4 wherein said first and second air locks comprises a pair of septae and said means to inject drilling fluid sample lots of fluid and remove gasses are syringes.

* * * * *